US011234914B2

(12) United States Patent
Osthoff et al.

(10) Patent No.: US 11,234,914 B2
(45) Date of Patent: Feb. 1, 2022

(54) MONOSUBSTITUTED UREA DERIVATIVES AS A SELF-TANNING SUBSTANCE

(71) Applicant: MERCK PATENT GMBH, Darmstadt (DE)

(72) Inventors: Julian Osthoff, Dieburg (DE); Hansjuergen Driller, Gross-Umstadt (DE); Christophe Carola, Bensheim (DE); Robin Back, Bensheim (DE); Michael Krohn, Lorsch (DE)

(73) Assignee: MERCK PATENT GMBH, Darmstadt (DE)

( * ) Notice: Subject to any disclaimer, the term of this patent is extended or adjusted under 35 U.S.C. 154(b) by 19 days.

(21) Appl. No.: 16/339,996

(22) PCT Filed: Oct. 2, 2017

(86) PCT No.: PCT/EP2017/074963
§ 371 (c)(1),
(2) Date: Apr. 5, 2019

(87) PCT Pub. No.: WO2018/065358
PCT Pub. Date: Apr. 12, 2018

(65) Prior Publication Data
US 2020/0038304 A1 Feb. 6, 2020

(30) Foreign Application Priority Data

Oct. 7, 2016 (DE) .................... 10 2016 011 953.5

(51) Int. Cl.
*A61K 8/42* (2006.01)
*A61Q 19/04* (2006.01)
*A61K 8/06* (2006.01)
*A61Q 19/08* (2006.01)

(52) U.S. Cl.
CPC ............... *A61K 8/42* (2013.01); *A61K 8/062* (2013.01); *A61K 8/064* (2013.01); *A61Q 19/04* (2013.01); *A61Q 19/08* (2013.01)

(58) Field of Classification Search
None
See application file for complete search history.

(56) References Cited

U.S. PATENT DOCUMENTS

| 3,728,454 | A | * | 4/1973 | Douros, Jr. | .......... | C07D 239/60 |
|---|---|---|---|---|---|---|
| | | | | | | 514/269 |
| 3,867,426 | A | * | 2/1975 | Olin | ....... | C07C 275/34 |
| | | | | | | 560/32 |
| 6,214,322 | B1 | * | 4/2001 | Castro | ...... | A61K 8/60 |
| | | | | | | 424/400 |
| 6,248,746 | B1 | | 8/2001 | Chasin et al. | | |
| 2004/0231069 | A1 | | 11/2004 | Carrascal et al. | | |
| 2007/0231279 | A1 | * | 10/2007 | Schulz | ...... | A61Q 3/00 |
| | | | | | | 424/59 |
| 2010/0129515 | A1 | | 5/2010 | Winkel et al. | | |
| 2016/0199276 | A1 | | 7/2016 | Plos et al. | | |

FOREIGN PATENT DOCUMENTS

| EP | 1454613 A1 * | 9/2004 | ............... A61K 8/42 |
|---|---|---|---|
| EP | 1454615 B1 | 10/2005 | |
| EP | 1454613 B1 | 8/2010 | |
| FR | 3004934 B1 | 9/2015 | |
| JP | 01149708 A * | 6/1989 | ............. A61Q 5/065 |
| WO | 07013811 A2 | 2/2007 | |
| WO | WO-2007013811 A2 * | 2/2007 | ........... A23L 27/204 |
| WO | 14174075 A2 | 10/2014 | |

OTHER PUBLICATIONS

Smith et al. (Food Technology, 2003, 57(5), 46-59.*
Colgate (https://www.colgate.com/en-us/oral-health/adult-oral-care/tongue-pigmentations-causes-and-treatment) no date available, no pagination.*
Mayo Clinic (https://www.mayoclinic.org/healthy-lifestyle/adult-health/in-depth/sunless-tanning/art-20046803) internet p. 1-2, Jun. 4, 2013.*
Borgna et al. "Preparation and study of the phytotoxic activity of N-aralkyl-substituted amides . . . " Farmaco, Ed. Sci. 1997, 32(11), 813-826. see also google translation paragraph that is attached as separate document.*
Wisebread (https://www.wisebread.com/19-money-saving-uses-for-mouthwash), no pagination, 2011.*
Seattletimes "mouthwash as acne treatment" https://www.seattletimes.com/seattle-news/health/mouthwash-as-an-acne-treatment/, no pagination, 2013.*
Borgna et al. "Preparation and study of the phytotoxic activity . . . " Farmaco, Ed. Soc. 1977, 32(11), 813-826. see also google translation paragraph that is included as separated document (Year: 1977).*
Wisebread (https://www.wisebread.com/19-money-saving-uses-for-mouthwash), no pagination, 2011 (Year: 2011).*
Seattletimes "Mouthwash as acne treatment" https://www.seattletimes.com/seattle-news/health/mouthwash-as-an-acne-treatment/, no pagination. 2013 (Year: 2013).*
International Search Report PCT/EP2017/074963 dated Jan. 8, 2019 (pp. 1-3).
Criton M et al: "Analogues of N-hydroxy-N'-phenylthiourea and N-hydroxy-N'-phenylurea as inhibitors of tyrosinase and melanin formation", Bioorganic & Medicinal Chemistry Letters, Pergamon, Amsterdam, NL, vol. 18, No. 12, Jun. 15, 2006 (Jun. 15, 2008), pp. 3607-3610, XP022707442, ISSN: 0960-894X.
David A Brown: "Skin pigmentation enhancers". Journal of Photochemistry and Photobiology B: Biology, vol. 63, No. 1-3, Oct. 1, 2001 (Oct. 1, 2001), pp. 148-161, XP055085922, ISSN: 1011-1344.
Schlossman ; Treated Pigments . . . . . : Cosmetics & Toiletries, vol. 105, Feb. 1990 (Feb. 1, 1990), pp. 53-54.

* cited by examiner

*Primary Examiner* — Erin E Hirt
(74) *Attorney, Agent, or Firm* — Millen White Zelano & Branigan; Richard J. Traverso

(57) ABSTRACT

The present invention relates to the use of monosubstiuted urea derivatives of the formula I as self-tanning substance, for increasing melanin synthesis, for improving melanin transport and/or improving the distribution of melanin in suprabasal layers, and to preparations comprising these urea derivatives.

18 Claims, No Drawings

MONOSUBSTITUTED UREA DERIVATIVES AS A SELF-TANNING SUBSTANCE

The present invention relates to the use of monosubstiuted urea derivatives of the formula I as self-tanning substance, for increasing melanin synthesis, for improving melanin transport and/or improving the distribution of melanin in suprabasal layers, and to preparations comprising these urea derivatives.

The trend away from refined paleness towards "healthy, sporty brown skin" has been uninterrupted for years. In order to achieve a tanned complexion, people expose their skin to sunlight, since this causes pigmentation due to melanin formation. However, the UV radiation in sunlight also has a damaging effect on the skin. Besides acute damage (sunburn), long-term damage occurs on excessive irradiation with light from the UVB region (wavelength 280-320 nm), such as, for example, an increased risk of contracting skin cancer. Excessive exposure to UVB and UVA radiation (wavelength: 320-400 nm) generates highly reactive free-radical species, which multiply further even after termination of the irradiation, and wrinkling and skin ageing occur as a consequence thereof.

Tanning (pigmentation) of the skin offers natural protection against the adverse consequences of sunlight. The epidermis contains individual pigment-forming cells, the melanocytes, besides the basal cells in its lowest layer, the basal layer. UV light stimulates the production of melanin in these cells, which is transported into the kerantinocytes (horny cells), where it becomes visible as a brown skin colour. Melanin protects the cell nuclei against further irradiation and the adverse effects it causes on the cell DNA.

Depending on the chemical composition of the pigments formed biochemically, a distinction is made between brownish-black eumelanin and reddish-yellow pheomelanin. The skin hue observed is determined by the ratio of these two types of melanin.

This pigment formation starting from the amino acid tyrosine is initiated predominantly by UVB radiation and is known as "indirect pigmentation". Its development runs over a number of days; the suntan obtained in this way lasts a few weeks. In the case of "direct pigmentation", which commences with the solar irradiation, predominantly colourless melanin precursors are oxidised by UVA radiation to dark-coloured melanin. Since this oxidation is reversible, it results in skin tanning which only lasts briefly.

Artificial tanning of the skin can be produced externally with the aid of make-up and orally by taking carotenoids.

Much more popular, however, is artificial tanning of the skin which can be achieved by the application of so-called self-tanning agents.

These compounds have, as a chemical structural feature, keto or aldehyde groups in the vicinity of alcohol functions and predominantly belong to the class of substances of the sugars. Particularly frequently employed self-tanning substances are 1,3-dihydroxyacetone (DHA), which is used in an amount of 700 t/a, and erythrulose.

Self-tanning agents can be reacted with the proteins and amino acids of the horny layer of the skin in the sense of a Maillard reaction or via a Michael addition, where polymers which give the skin a brownish hue form via a reaction route which has not yet been clarified completely. This reaction is complete after about 4 to 6 hours. The tan achieved in this way cannot be washed off and is only removed with the normal skin desquamation.

However, these coloured products do not themselves have UV-absorbent properties, meaning that additional sun protection (clothing, hat, application of UV filters) is necessary on exposure to the sun. In contrast to "sun-tanned" skin, skin tanned in this way is not protected against sunburn.

There therefore continues to be a demand for dermatologically tolerated skin-colouring substances which are suitable for use in cosmetic and/or dermatological preparations or medical devices and which enhance the natural tanning of the skin by increasing melanin synthesis and at the same time enable better inherent skin protection or sun protection, in particular against UVB radiation.

The object on which the present invention is based therefore consisted in the provision of novel self-tanning substances having improved properties.

Surprisingly, it has now been established that certain monosubstituted urea derivatives are suitable as self-tanning substances, in particular as self-tanning substances which facilitate natural tanning of the skin by affecting melanin synthesis and/or melanin distribution.

For the purposes of the invention, the term self-tanning active compound is used synonymously with self-tanning substance or self-tanner substance.

Marc Criton et al, Bioorganic & Medicinal Chemistry Letters 2008, 18, 3607-3610, disclose structurally related compounds of N-hydroxy-N'-phenylthiourea and of N-hydroxy-N'-phenylurea, which are also described as skin lighteners, in particular as tyrosinase inhibitors.

The present invention therefore relates firstly to the use of compounds of the formula I,

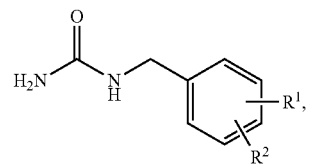

where $R^1$ and $R^2$ stand, independently of one another, for

H,

OH, straight-chain or branched O—($C_1$- to $C_6$-alkyl), where $R^1$ and $R^2$ may also together form an unsubstituted or substituted five-membered ring, in which one or two non-adjacent $CH_2$ groups may be replaced by O and which may be substituted by at least one straight-chain or branched alkyl group having 1 to 6 C atoms, and/or salts, tautomers, conformers and/or solvates thereof, including mixtures thereof in all ratios, als self-tanning substance.

The invention furthermore relates to the use of compounds of the formula I,

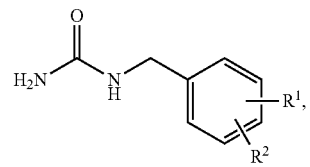

where
R¹ and R² stand, independently of one another, for
H,
OH,
straight-chain or branched O—(C₁- to C₆-alkyl), where R¹ and R² may also together form an unsubstituted or substituted five-membered ring, in which one or two non-adjacent CH₂ groups may be replaced by O and which may be substituted by at least one straight-chain or branched alkyl group having 1 to 6 C atoms,
and/or salts, tautomers, conformers and/or solvates thereof, including mixtures thereof in all ratios, for increasing melanin synthesis, for improving melanin transpart and/or for improving the distribution of melanin in suprabasal layers.

For the purposes of the invention, the compounds of the formula I are defined such that they are also taken to mean pharmaceutically or cosmetically usable salts, hydrates, solvates, tautomers and conformers. Solvates of the compounds are taken to mean adductions of inert solvent molecules onto the compounds, which form owing to their mutual attractive force. Solvates are, for example, mono- or dihydrates or alcoholates.

The preferred salts here include, in particular, alkali and alkaline-earth metal salts, zinc salts and ammonium salts, but in particular sodium salts and potassium salts.

Tautomers denote molecules having the same empirical formula whose atoms are linked differently and which rapidly interconvert due to the migration of individual atoms or atom groups, i.e. the two isomers are in rapid chemical equilibrium with one another.

The conformation of an organic molecule describes the spatial arrangement of its rotatable bonds at the carbon atoms. It fully describes the three-dimensional spatial coordinates of all atoms of the molecule. Molecules having the same arrangement of atoms, but which differ in the specific arrangement of the atoms and lie at an energy minimum, are called conformers. The term rotamer is also common as a synonym therefor.

A straight-chain or branched alkyl group having 1 to 6 C atoms is, for example, methyl, ethyl, isopropyl, n-propyl, n-butyl, sec-butyl or tert-butyl, pentyl, 1-, 2- or 3-methylbutyl, 1,1-, 1,2- or 2,2-dimethylpropyl, 1-ethylpropyl or n-hexyl.

The term "C₁- to C₆-alkyl" used here denotes a straight-chain or branched alkyl group having 1 to 6 C atoms, as described above.

The term "O—(C₁- to C₆-alkyl)" used here denotes a straight-chain or branched alkoxy group having 1 to 6 C atoms, where the alkyl group described above is correspondingly bonded to an O atom.

Compounds of the formula I are preferably used if the substituent R¹ in formula I preferably stands for H, OH or a straight-chain or branched alkoxy group having 1 to 4 C atoms. The substituent R¹ in compounds of the formula I particularly preferably stands for H, OH or OCH₃.

The invention therefore furthermore relates to the use of compounds of the formula I, as described above, in which the substituent R¹ stands for H, OH or a straight-chain or branched alkoxy group having 1 to 4 C atoms, or preferably stands for H, OH or OCH₃.

Compounds of the formula I are preferably used if the substituent R² in formula I stands for H, OH or a straight-chain or branched alkoxy group having 1 to 4 C atoms. The substituent R² in compounds of the formula I particularly preferably stands for H, OH or OCH₃.

The invention therefore furthermore relates to the use of compounds of the formula I, as described above, in which the substituent R² stands for H, OH or a straight-chain or branched alkoxy group having 1 to 4 C atoms, or preferably stands for H, OH or OCH₃.

As described above, the substituents R¹ and R² in compounds of the formula I may together form a five-membered ring, in which one or two non-adjacent CH₂ groups may be replaced by O and which may be substituted by at least one straight-chain or branched alkyl group having 1 to 6 C atoms.

In a particularly preferred embodiment of the present invention, compounds of the formula I are used in which the substituents R¹ and R² in formula I together preferably form a five-membered ring containing two O atoms, which may be substituted by one or two straight-chain or branched alkyl group(s) having 1 to 6 C atoms. A five-membered ring formed in this way is preferably substituted by one or two methyl group(s) or unsubstituted.

The invention therefore furthermore relates to the use of compounds of the formula I, as described above, in which the substituents R¹ and R² together form a five-membered ring containing two O atoms, which may be substituted by one or two straight-chain or branched alkyl group(s) having 1 to 6 C atoms.

The substituent R¹ is preferably in position 3 of the benzyl ring; the substituent R² is preferably in position 4 of the benzyl ring, visualised by the formula I-1:

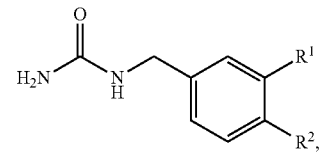

I-1 where R¹ and R² have a meaning in each case given above or a preferably given meaning.

Examples of compounds of the formula I or of the formula I-1 are the compounds Ia to Ik:

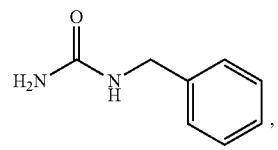

Ia

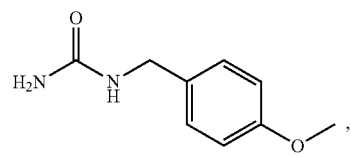

Ib

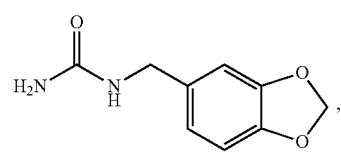

Ic

-continued

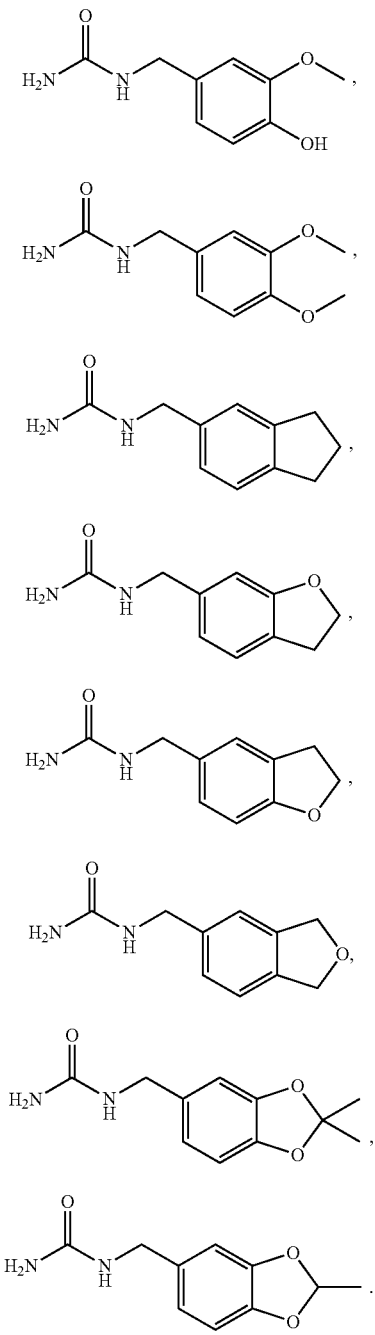

For the use according to the invention, as described above, the compound of the formula I is particularly preferably selected from the compounds of the formula Ia, Ib, Ic, Id and Ie,

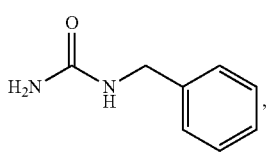

-continued

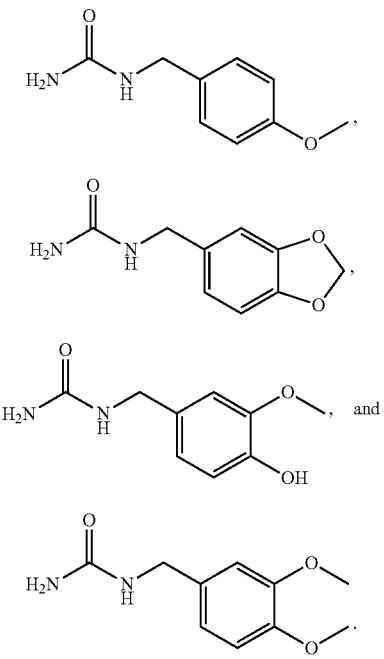

For the use according to the invention, as described above, at least one compound of the formula Ia, Ib and/or Ic is very particularly preferably selected. From the group of the compounds of the formula Ia, Ib and/or Ic, the compound of the formula Ic is preferred.

The compounds of the formula I are commercially available or can be prepared by syntheses known to the person skilled in the art. They can be prepared, for example, by reaction of a corresponding amine of the formula II

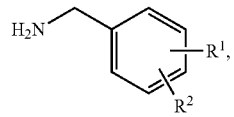

in which the substituents $R^1$ and $R^2$ have one of the meanings indicated or preferably indicated above, with urea with acid catalysis.

A person skilled in the art in the area of organic synthesis will easily be able to find the reaction condition necessary for this purpose in the generally available literature on organic reactions. Examples of reaction conditions are described in the experimental part.

The reaction is preferably carried out in water. The reaction can optionally be carried out in organic solvents or in mixtures of organic solvents with water.

The reaction is preferably carried out with acid catalysis using concentrated hydrochloric acid. The reaction temperature is between 60° C. and 130° C. The reaction is particularly preferably carried out at the boiling point of the solvent or solvent mixture. The reaction is often followed by suitable purification.

Suitable purification steps include separating off readily volatile components by distillation or condensation, extraction with an organic solvent, precipitation by addition of an organic solvent, salt exchange or a combination of these methods. Any known separation method can be used or combined for this purpose. In general, the desired reaction product precipitates out of the reaction mixture and is separated off and purified correspondingly.

Further details are given in the examples, which also apply correspondingly to the general synthesis description.

Compounds of the formula I surprisingly increase melanin synthesis and/or improve melanin transport from the melanocytes to the keratinocytes and/or distribute melanin better in suprabasal layers. A compound of the formula I can therefore also be referred to as melanogenesis promoter or propigmentation active compound. The compounds of the formula I preferably increase melanin synthesis. This affects the colour of the skin and causes a tanning effect. This property is surprising inasmuch as the opposite effect, namely inhibition of melanin synthesis, is described for similar compounds.

Besides the tanning action, the compounds of the formula I are also well tolerated by the skin. In addition, preferred compounds of those described here are colourless or only weakly coloured and thus do not lead to discolorations of the preparations, or only do so to a slight extent. In addition, the preferred compounds have improved solubility in cosmetic oils.

In order that the compounds of the formula I are able to develop their positive action on the skin particularly well, it may be preferred to allow the compounds of the formula I, as described above, to penetrate into deeper skin layers. A number of possibilities are available to this end. Firstly, the compounds of the formula I may have adequate lipophilicity in order to be able to penetrate through the outer skin layer into epidermal layers. As a further possibility, corresponding transport means, for example liposomes, which enable transport of the compounds of the formula I through the outer skin layers, may also be provided in the topical preparation. Finally, systemic transport of the compounds of the formula I is also conceivable.

The uses according to the invention preferably take place non-therapeutically.

The present invention furthermore relates to a preparation comprising a vehicle which is suitable for topical applications and at least one compound of the formula I in an amount of 0.01 to 10% by weight,

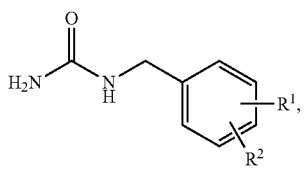

I where
$R^1$ and $R^2$ stand, independently of one another, for
H,
OH,
straight-chain or branched O—($C_1$- to $C_6$-alkyl),
where $R^1$ and $R^2$ may also together form an unsubstituted or substituted five-membered ring, in which one or two non-adjacent $CH_2$ groups may be replaced by O and which may be substituted by at least one straight-chain or branched alkyl group having 1 to 6 C atoms, and/or salts, tautomers, conformers and/or solvates thereof, including mixtures thereof in all ratios, or a preferred compound of the formula I, as described above.

The topically usable preparation here is usually cosmetic or dermatological formulations or medical devices. In this case, the preparations comprise a cosmetically or dermatologically suitable vehicle or a vehicle which is suitable for a medical device and, depending on the desired property profile, optionally further suitable ingredients.

For the purposes of the present invention, the term composition or formulation is also used synonymously alongside the term preparation.

"Can be applied topically" in the sense of the invention means that the preparation is used externally and locally, i.e. that the preparation must be suitable for, for example, application to the skin.

The preparations may include or comprise, essentially consist of or consist of the said requisite or optional constituents. All compounds or components which can be used in the preparations are either known and commercially available or can be synthesised by known processes.

The preparation is preferably a cosmetic or dermatological preparation; the preparation is particularly preferably a cosmetic preparation.

The at least one compound of the formula I, as described above or as preferably described is employed in the preparations according to the invention in amounts of 0.01 to 10% by weight, preferably in amounts of 0.05 to 10% by weight, particularly preferably in amounts of 0.1% by weight to 5% by weight and very particularly preferably in amounts of 0.5 to 2% by weight, based on the total amount of the preparation. The person skilled in the art is presented with absolutely no difficulties here in selecting the amounts appropriately depending on the intended action of the preparation.

Furthermore, the preparations according to the invention may comprise at least one further self-tanning substance as further ingredient. This can be either a self-tanning agent which reacts with the amino acids of the skin in the sense of a Maillard reaction or via a Michael addition, or a melanogenesis promoter or propigmentation active compound which promotes the natural tanning of the skin.

Advantageous self-tanning substances which can be employed are, inter alia: 1,3-dihydroxyacetone, glycerolaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone). Very particular preference is given to 1,3-dihydroxyacetone, erythrulose or a combination thereof.

Propigmentation substances can in principle be all active compounds known to the person skilled in the art. Examples thereof are glycyrrhetinic acid, melanocyte-stimulating hormone (alpha-MSH), peptide analogues, thymidine dinucleotides, L-tyrosine and esters thereof or bicyclic monoterpenediols (described in Brown et al., Photochemistry and Photobiology B: Biology 63 (2001) 148-161), or hexadecanoic acid 5-hydroxy-2-methyl-4-oxo-4H-chromen-7-yl ester, which is marketed by Merck under the trade name RonaCare® Bronzyl™. Particularly suitable active compounds for combination with at least one compound of the formula I, as described above, are 1,3-dihydroxyacetone, erythrulose and/or hexadecanoic acid 5-hydroxy-2-methyl-4-oxo-4H-chromen-7-yl ester.

The at least one further self-tanning substance is preferably present in the preparation in an amount of 0.01 to 20% by weight, particularly preferably in an amount of 0.1 to 15% by weight and very particularly preferably in an amount of 0.2 to 8% by weight, based on the total amount of the preparation.

Preparations having self-tanner properties, in particular those which comprise dihydroxyacetone, tend towards malodours on application to the human skin, which are thought to be caused by degradation products of dihydroxyacetone itself or by products of side reactions and which are regarded as unpleasant by some users. It has been found that these malodours are prevented on use of formaldehyde scavengers and/or flavonoids. The preparation according to the invention may therefore preferably also comprise formaldehyde scavengers and optionally flavonoids for improving the odour.

The formaldehyde scavenger is preferably selected from the group alkali metal, alkaline-earth metal or ammonium disulfite. Particular preference is given to a preparation which comprises, in combination DHA Plus, a mixture of DHA, sodium disulfite and magnesium stearate.

DHA Plus is a product mixture which comprises sodium metabisulfite, synonymous with $Na_2S_2O_5$ or INCI: sodium disulfite, for the masking, elimination or neutralisation of formaldehyde. The addition of sodium metabisulfite in finished formulations results in significant reduction or suppression of the unpleasant odour. DHA Plus is marketed by Merck, Darmstadt.

The preparation according to the invention comprising at least one compound of the formula I, as described above with the substituents indicated and also preferably mentioned, and dihydroxyacetone as self tanner, may particularly preferably comprise flavonoids for improving the odour and optionally for accelerating tanning.

The flavonoid here additionally acts as stabiliser for the self-tanner or the self-tanning substances and/or reduces or prevents or improves storage-dependent malodours, which may also arise due to additives or assistants present.

This is preferably a flavonoid in which one or more phenolic hydroxyl groups have been blocked by etherification or esterification. For example, hydroxyethyl-substituted flavonoids, such as, preferably, troxerutin, troxequercetin, troxeisoquercetin or troxeluteolin, and flavonoid sulfates or flavonoid phosphates, such as, preferably, rutin sulfates, have proven to be particularly highly suitable flavonoids here. In the sense of this use, particular preference is given to rutin sulfate and troxerutin. Very particular preference is given to the use of troxerutin.

The preferred flavonoids have a non-positively charged flavan skeleton. It is thought that metal ions, such as, for example, $Fe^{2+}/Cu^{2+}$, are complexed by these flavonoids and auto-oxidation processes in the case of fragrances or compounds whose degradation results in malodours are thus prevented or reduced.

Particular preference is given to a preparation which, besides at least one compound of the formula I, as described above or preferably described, comprises DHA Rapid. DHA Rapid is a product mixture comprising dihydroxyacetone and troxerutin, from Merck, Darmstadt. This particularly preferred preparation may optionally also comprise a formaldehyde scavenger, for example sodium disulfite.

Corresponding premixes and preparations which comprise formaldehyde scavengers and optionally flavonoids in order to improve the odour on the skin are described in the German patent application DE 10 2007 013 368 A1.

Besides the compounds of the formula I, as described above or described as preferred, the preparations according to the invention may additionally also comprise at least one UV filter.

Organic UV filters, so-called hydrophilic or lipophilic sun-protection filters, which are effective in the UVA region and/or UVB region and(/or IR and/or VIS region (absorbers). These substances can be selected, in particular, from dibenzoylmethane derivatives, cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO—93/04665. Further examples of organic filters are indicated in the patent application EP-A 0 487 404. The said UV filters are usually named below in accordance with INCI nomenclature.

Particularly suitable for a combination are:

dibenzoylmethane derivatives, for example 4-isopropyldibenzoylmethane and 4,4'-methoxy-tert-butyldibenzoylmethane, which are described in the laid-open specifications FR-A-2 326 405, FR-A-2 440 933 and EP-A-0 114 607. 4,4'-Methoxy-tert-butyldibenzoylmethane is marketed, for example, by Merk under the name Eusolex 9020.

Para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed under the name "Uvinul P25" by BASF.

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β, β-Diphenylacrylate derivatives: Octocrylene, for example marketed by Merck under the name "Eusolex OCR", "Uvinul N539" from BASF, Etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl) benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzo-triazolyl)tetramethylbutylphenol in solid form, for example marketed by Fairmount Chemical under the name "MIXXIM BB/100", or in micronised form as an aqueous dispersion, for example marketed by BASF under the name "Tinosorb M".

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl 4'-aminobenzalmalonate)s-triazine or 2,4,6-tris(biphenyl)-1,3,5-triazine. marketed as Tinosorb A2B by BASF, 2,2'-[6-(4-methoxyphenyl)-1,3,5-triazine-2,4-diyl]bis[5-(2-ethylhexyl)oxy]phenol, marketed as Tinosorb S by BASF, N2,N4-bis[4-[5-(1,1-dimethylpropyl)-2-benzoxazolyl]phenyl]-N6-(2-ethylhexyl)-1,3,5-triazine-2,4,6-triamine marketed as Uvasorb K 2A by Sigma 3V.

Anthraniline derivatives: Menthyl anthranilate, for example marketed by Symrise under the name "Neo Heliopan MA".

Imidazole derivatives: Ethylhexyldimethoxybenzylidene-dioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl) benzoxazol-2-yl(4-phenyl) imino]-6-(2-ethylhexyl)imino-1,3,5-triazine, for example marketed by Sigma 3V under the name Uvasorb K2A, and mixtures comprising this.

Piperazine derivatives, such as, for example, the compound

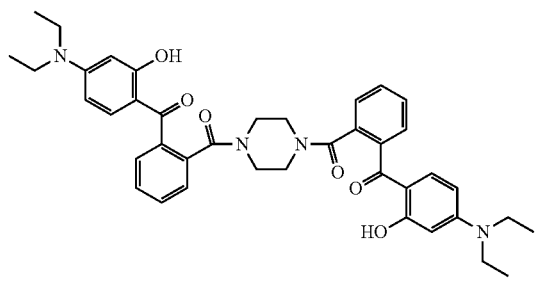 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

or the UV filters of the following structures

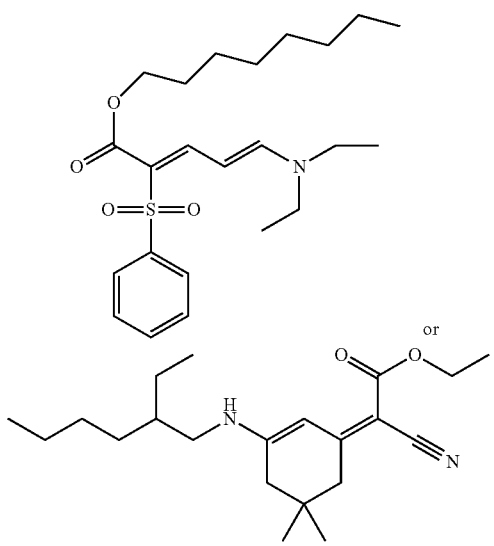

It is also possible to use UV filters based on polysiloxane copolymers having a random distribution in accordance with the following formula, where, for example, a=1.2; b=58 and c=2.8:

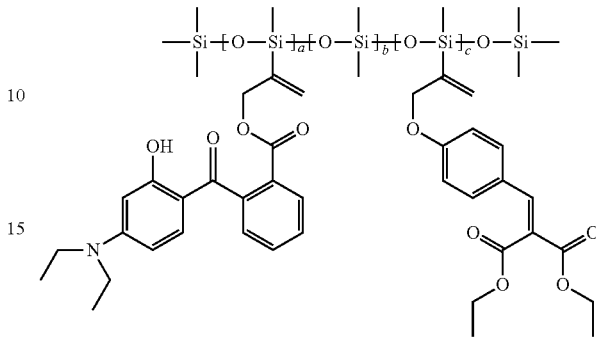

The compounds listed should only be regarded as examples. It is of course also possible to use other UV filters.

Suitable organic UV-protecting substances can preferably be selected from the following list: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetra-sulfonate, Methylenebis(benzotriazolyl)tetramethylbutylphenol, Butyl Methoxydibenzoylmethane, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-bis[5-1(dimethylpropyl)benzoxazol-2-yl (4-phenyl) imino]-6-(2-ethylhexyl)imino-1,3,5-triazine and mixtures thereof.

These organic UV filters are generally incorporated into formulations in an amount of 0.01 percent by weight to 20 percent by weight, preferably 1% by weight-10% by weight.

Besides the compounds of the formula I and the optional organic UV filters, as described above, the preparations may comprise further inorganic UV filters, so-called particulate UV filters.

These combinations with particulate UV filters are possible both as powder and also as dispersion or paste of the following types.

Preference is given here both to those from the group of the titanium dioxides, such as, for example, coated titanium dioxide (for example Eusolex® T-2000, Eusolex®T-AQUA, Eusolex®T-AVO, Eusolex®T-PRO, Eusolex® T-EASY), zinc oxides (for example Sachtotee), iron oxides or also cerium oxides and/or zirconium oxides.

Furthermore, combinations with pigmentary titanium dioxide or zinc oxide are also possible, where the particle size of these pigments are greater than or equal to 200 nm, for example Hombitan® FG or Hombitan® FF-Pharma.

It may furthermore be preferred for the preparations to comprise inorganic UV filters which have been aftertreated by conventional methods, as described, for example, in Cosmetics & Toiletries, February 1990, Vol. 105, pp. 53 64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

These inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form.

The capsules in preparations to be employed in accordance with the invention are preferably present in amounts which ensure that the encapsulated UV filters are present in the preparation in the percent by weight ratios indicated above.

The preparations described, which in accordance with the invention comprise the at least one compound of the formula I, may furthermore also comprise coloured pigments, where the layer structure of the pigments is not limited.

The coloured pigment should preferably be skin-coloured or brownish on use of 0.5 to 5% by weight. The selection of a corresponding pigment is familiar to the person skilled in the art.

Preferred preparations may likewise comprise at least one further cosmetic active compound, for example selected from antioxidants, anti-ageing, antiwrinkle, anti-dandruff, anti-acne, anti-cellulite active compounds, deodorants or vitamins.

The protective action of preparations against oxidative stress or against the effect of free radicals can be improved if the preparations comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles, (for ecample urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysta sulfoximine, buthionine sulfones, penta-, hexa- and heptathionine sulfoximine) in very low tolerated doses (for example pmol to μmol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA, pentasodium ethylenediamine tetramethylene phosphonate and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, α-glycosyl-rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are also compounds of the formulae A or B

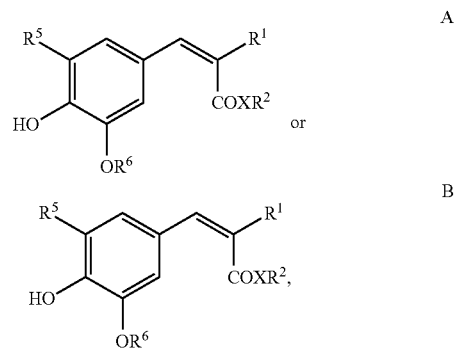

in which
$R^1$ can be selected from the group —C(O)CH$_3$, —CO$_2$R$^3$, —C(O)NH$_2$ and —C(O)N(R$^4$)$_2$,
X denotes O or NH,'
$R^2$ denotes linear or branched alkyl having 1 to 30 C atoms,
$R^3$ denotes linear or branched alkyl having 1 to 20 C atoms,
$R^4$ in each case, independently of one another, denotes H or linear or branched alkyl having 1 to 8 C atoms,
$R^5$ denotes H, linear or branched alkyl having 1 to 8 C atoms or linear or branched alkoxy having 1 to 8 C atoms and
$R^6$ denotes linear or branched alkyl having 1 to 8 C atoms,
preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxybenzyl)malonate (for example RonaCare® AP).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such preparations with the compounds according to the invention in percent by weight ratios in the range from 1000:1 to 1:1000, preferably in percent by weight ratios of 100:1 to 1:100.

Suitable anti-ageing active compounds, in particular for skin-care preparations, are preferably so-called compatible solutes. The compatible solutes are preferably substances selected from the group consisting of pyrimidine-carboxylic acids (such as ectoin and hydroxyectoin), proline, betaine, glutamine, cyclic diphosphoglycerate, N-acetylornithine, trimethylamine N-oxide di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) dimannosyl diinositol phosphate (DMIP) or an optical isomer or derivative, for example an acid, salt or ester, of these compounds, and combinations thereof.

Additionally, anti-aging active compounds which can be used are products from Merck, such as, for example, 5,7-dihydroxy-2-methylchromone, marketed under the trade name RonaCare®Luremin®, or the commercial products RonaCare®ASCIII®, RonaCare®RenouMer, RonaCare®Nicotinamide, RonaCare®VTA, RonaCare®Poppy SE, RonaCare®Isoquercetin or RonaCare®Cyclopeptide 5.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or preparations in ranges from 0.01 to 5.0% by weight, based on the total weight. Nutrition-physiological applications are oriented towards the respective recommended vitamin requirement.

The retinoids described are at the same time also effective anti-cellulite active compounds. A likewise known anti-cellulite active compound is caffeine.

The preparations may preferably comprise assistants, such as, for example, cosmetic oils (for example Caprylic/Capric Triglycerides, C12-15 alkyl Benzoate, isopropyl myristate, arylalkyl benzoates, such as, for example, phenethyl benzoate (X-Tend 226) or oil components of the Cosmacol brand, such as Dimyristyl Tartrate, Tri C14-C15 Alkyl Citrate, C12-C13 Alkyl Lactate, Tridecyl Salicylate, C12-C13 Alkyl Octanoate, C12-C13 Alkyl Malate, C12-C13 Alkyl Citrate, C12-C13 Alkyl Tartrate), or polar-protic assistants (for example propylene glycol, glycerol, isopropanol, ethanol) or so-called solubilisers (for example Butylphthalimide, Isopropylphthalimide, Dimethylisosorbide). Very particularly preferred cosmetic oils are C12-C13 Alkyl Lactate, commercially available as Cosmacol ELI and phenethyl benzoate, commercially available as X-Tend 226.

The present invention also relates to a process for the preparation of a preparation, as described above, characterised in that at least one compound of the formula I is mixed with a vehicle which is suitable for topical preparations and optionally with assistants and or fillers. Suitable vehicles and assistants or fillers are described in detail in the following part.

The said constituents of the preparation can be incorporated in the usual manner, with the aid of techniques which are well known to the person skilled in the art.

Preparations are suitable for external use, for example can be sprayed onto the skin as cream or milk (O/W, W/O, O/W/O, W/O/W), as lotion or emulsion, in the form of oily-alcoholic, oily-aqueous or aqueous-alcoholic gels or solutions. They can be in the form of solid sticks or formulated as aerosol.

The following, for example, may be mentioned as application form of the preparations to be employed: solutions, suspensions, emulsions, PIT emulsions, pastes, ointments, gels, creams, lotions, powders, soaps, surfactant-containing cleansing preparations, oils, aerosols plasters, compresses, bandages and sprays.

Preferred assistants originate from the group of preservatives, stabilisers, solubilisers, colorants, odour improvers, thickeners, plasticisers, humectants, interface-active agents, emulsifiers, preservatives, antifoaming agents, perfumes, waxes, lanolin, propellants and other ingredients usually used in cosmetics.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluoro-carbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, XTend 226 (L'Oréal), glycerol fatty acid esters, polyethylene glycols and fatty acid esters of sorbitan, or mixtures of these substances.

A preferred solubiliser in general is 2-isopropyl-5-methylcyclohexane-carbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium meta-hydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

The lipid phase may advantageously be selected from the following group of substances:
mineral oils, mineral waxes
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acid and saturated and/or unsaturated, branched and/or unbranched alcohols having a chain length of 3 to 30 C atoms.

The oil phase may furthermore advantageously be selected from the group branched and unbranched hydrocarbons and hydrocarbon waxes, silicone oils, dialkyl ethers, the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may, for example, advantageously be selected from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as sole lipid component of the oil phase.

The aqueous phase of the preparations to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

In a preferred embodiment, the preparations to be employed comprise hydrophilic surfactants. The hydrophilic surfactants are preferably selected from the group of the alkylglucosides, acyl lactylates, betaines and coconut amphoacetates.

Emulsifiers that can be used are, for example, known W/O and O/W emulsifiers. It is advantageous to use further conventional co-emulsifiers in the preferred O/W emulsions.

The dispersant or solubiliser used can be an oil, wax or other fatty bodies, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion which is in the form of a protective cream or milk and comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The preparation may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is generally made of the customary propellants, such as alkanes, fluoroalkanes and chlorofluoroalkanes, preferably alkanes.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference. The weight percent ratios of the individual ingredients in the preparations of the examples expressly belong to the disclosure content of the description and can therefore be utilised as features.

Further important features and advantages of the invention arise from the sub-claims and from the examples.

The examples are intended to explain the present invention in greater detail without restricting the scope thereof.

It goes without saying that the features mentioned above and still to be explained below can be used not only in the combination indicated in each case, but also in other combinations or alone, without leaving the scope of the present invention.

EXAMPLES

Example 1

Synthesis of Benzylurea (Ia)

6.00 g of benzylamine (56 mmol) and 13.45 g of urea (224 mmol) are weighed out successively into a 50 mL round-bottomed flask. 25 mL of water are subsequently added via a volumetric flask. The reaction solution is stirred for 5 minutes, 0.1-0.5 mL of concentrated hydrochloric acid are added, and the mixture is boiled under reflux for 3 hours.

The reaction mixture is then cooled, and the product crystallises out at room temperature. 50 mL of water are added to the reaction mixture, and the precipitate is filtered off and washed with 4×15 mL of water and 3×10 mL of EtOH. The crude product is dried at 40° C. in a vacuum drying cabinet (50 mbar).

Yield: 6.81 g (82% of theory).

1H-NMR (500 MHz, DMSO) δ[ppm]=4.19 (d, 2H, $CH_2$—NH); 5.51 (s, 2H, $NH_2$); 6.41 (t, 1H, NH); 7.28 (ddt, 5H, aromatic).

Example 2

Synthesis of (4-methoxybenzyl)urea (Ib)

1.50 g of 4-methoxybenzylamine (10.72 mmol) and 2.57 g of urea (42.86 mmol) are reacted analogously to Example 1. The crude product is recrystallised from ethanol in the ratio 1:6 (substance: solvent).

Yield: 0.72 g (37% of theory).

1H-NMR (500 MHz, DMSO) δ[ppm]=3.72 (s, 3H, $CH_3$—O); 4.10 (d, 2H, $CH_2$—NH); 5.46 (s, 2H, $NH_2$); 6.30 (t, 1H, NH) 6.86 (d, 2H, aromatic); 7.17 (d, 2H, aromatic).

Example 3

Synthesis of benzo[1,3]dioxol-5ylmethylurea (Ic)

2.50 g of piperonylamine (16.04 mmol) and 3.85 g of urea (64.17 mmol) are reacted analogously to Example 1.

Yield: 2.87 g (88% of theory).

1H-NMR (500 MHz, DMSO) δ[ppm]=4.09 (d, 2H, $CH_2$—NH); 5.98 (s, 2H, O—$CH_2$—O); 5.48 (s, 2H, $NH_2$); 6.33 (t, 1H, NH) 6.72 (d, 1H, aromatic); 6.84 (dt, 2H, aromatic).z

Example 4

Synthesis of (4-hydroxy-3-methoxybenzyl)urea (Id)

2.00 g of 4-(aminomethyl)-2-methoxyphenol (10.44 mmol) and 2.00 g of urea (33.30 mmol) are reacted analogously to Example 1.

Yield: 1.56 g (76% of theory).

1H-NMR (500 MHz, DMSO) δ[ppm]=3.75 (s, 3H, $CH_3$—O); 4.07 (s, 2H, $CH_2$_NH); 5.48 (s, 2H, $NH_2$); 8.75 (s, 1H, NH); 6.65 (d, 1H, aromatic) 6.72 (d, 1H, aromatic); 6.82 (s, 1H, aromatic); 12.5 (s, 1H, OH-aromatic)

Example 5

Synthesis of (3,4-dimethoxybenzyl)urea (Ie)

2.50 g of 3,4-dimethoxybenzylamine (14.50 mmol) and 3.48 g of urea (58 mmol) are reacted analogously to Example 1.

Yield: 2.15 g (71% of theory).

1H-NMR (500 MHz, DMSO) δ[ppm]=3.73 (2s, 6H, $CH_3$—O); 4.10 (d, 2H, $CH_2$—NH); 5.47 (s, 2H, $NH_2$); 6.30 (t, 1H, NH) 6.75-6.90 (2d, 1s, 3H, aromatic).

Example 6

Evaluation of the Synthesis of Melanin in a Cell Culture Model Containing Two Cell Types (Co-Culture), Firstly Normal Human Epidermal KeratinoCytes (NHEK) and Secondly Normal Human Epidermal Melanocytes, Lightly Pigmented (NHEM-LP)

The two cell types NHEK and NHEM-LP (NHEK: NHEM-LP) are employed in a ratio of 2:1.

The culture medium consists of the media keratinocyte-SFM (2 parts by volume) and medium M254 (1 part by volume).

Keratinocyte-SFM contains 0.25 ng/ml of epidermal growth factor (EGF), 25 μg/ml of pituitary extract (PE) and 25 μg/ml of gentamycin and was purchased from Thermo Fisher Scientific.

M254 contains PMA-free HMGS-2, 5 μg/ml of insulin, 50 U/ml of penicillin, 50 μg/ml of streptomycin and 25 μg/ml of gentamycin and was purchased from Thermo Fisher Scientific.

IBMX denotes the compound 3-isobutyl-1-methylxanthine.

Cell Culture and Treatment

NHEK and NHEM-LP were incubated in the culture medium in microtitre plates (24-well plates) for 24 hours (37° C., 5% $CO_2$). The culture medium was removed and replaced by an assay medium which contained the culture medium and compounds Ia, Ib and Ic to be tested or alternatively no test substance, the reference L-tyrosine (1 mM), 200 μM of IBMX or the solvent control 0.1% of THF, 0.15% of THF. Compounds Ia, Ib and Ic are added as solution (0.15% in THF). After replacement of the assay medium, the cells were incubated again for 240 hours (10 days). On days 3 and 7, assay medium was again added. All experimental investigations were carried out using a triple determination. After the end of the incubation, the melanin was extracted by cell lysis with 0.5 N NaOH. The optical density (OD) of each sample was measured at 405 nm. The melanin quantity was calculated from melanin standards (standard curve 0.39 to 100 μg/ml of melanin).

Result

None of the solvent controls exhibited an influence on the melanin synthesis. Compound Ia, which was tested at 45 μM, stimulates melanin synthesis by 17%.

Compound Ib, which was tested at 45 μM, stimulates melanin synthesis by 18%.

Compound Ic, which was tested at 20 μM and 30 μM, exhibits a concentration-dependent stimulating effect on melanin synthesis by 23% or 44%.

Example 7

Evaluation of the Tanning Properties In Vitro on Reconstructed Epidermis

In this study, the tanning properties of compound Ic are investigated in vitro on 3D melanized reconstructed human epidermis (RHEs-MEL). The compound IBMX (3-isobutyl-1-methylxanthine) 100 μM is employed as positive control. Compound Ic is employed 25 μM and 12.5 M. Untreated reconstructed skin is used as negative control. The in vitro skin is treated systemically with the compounds to be investigated in a culture medium for 10 days and then analysed.

Result

Compound Ic has comparably good properties as IBMX at 100 μM. This is evident for both concentrations, both in the reduction of the ITA value (ITA=individual typology angle), the visual colour difference and the increased amount of melanin.

Example 8

O/W Formulation

| Constituents/trade name | Source of supply | INCI | [% by wt.] |
|---|---|---|---|
| A | | | |
| Marlipal 1618/11 | (1) | CETEARETH-11 | 3 |
| Lanette O | (2) | CETEARYLALCOHOL | 7 |
| Luvitol EHO | (3) | CETEARYLOCTANOATE | 5 |
| Tegosoft TN | (4) | C12-15 ALKYLBENZOATE | 2.5 |
| Miglyol 812 N | (1) | CAPRYLIC/CAPRIC TRIGLYCERIDE | 2.5 |
| Propyl 4-hydroxybenzoate | (5) | PROPYLPARABEN | 0.05 |
| Compound Ia, Ib, Ic, Id or Ie | | | 0.5 |
| B | | | |
| 1,2-Propanediol | (5) | PROPYLENE GLYCOL | 4 |
| Methyl 4-hydroxybenzoate | (5) | METHYLPARABEN | 0.15 |
| Water, demineralised | | AQUA (WATER) | to 100 |
| Water, demineralised | | | 10 |
| Total | | | 100.00 |

Preparation Process

Firstly, phase A is warmed to 75° C. and phase B to 80° C. Phase B is then slowly added to phase A with stirring and stirred until a homogeneous mixture forms.

Sources of Supply (1) Sasol Germany GmbH (2) Cognis GmbH (3) BASF SE
(4) Evonik Goldschmidt GmbH (5) Merck KGaA/Rona ®

Example 9

O/W Formulation

| Constituents/trade name | Source of supply | INCI | [% by wt.] |
|---|---|---|---|
| A | | | |
| Tego Care 150 | (1) | GLYCERYL STEARATE, STEARETH-25, CETETH-20, STEARYL ALCOHOL | 8 |
| Lanette O | (2) | CETEARYL ALCOHOL | 1.5 |
| Luvitol EHO | (3) | CETEARYL OCTANOATE | 5 |
| Miglyol 812 N | (4) | CAPRYLIC/CAPRIC TRIGLYCERIDE | 5 |
| Paraffin liquid | (5) | PARAFFINUM LIQUIDUM (MINERAL OIL) | 3 |
| AbilWax 2434 | (1) | STEAROXY DIMETHICONE | 1.6 |
| Dow Corning 200 Fluid (350 cs) | (6) | DIMETHICONE | 0.5 |
| Propyl 4-hydroxybenzoate | (5) | PROPYLLPARABEN | 0.05 |
| 5,7-Dihydroxy-2-methyl-chromone | (5) | | 0.2 |
| B | | | |
| 1,2-Propanediol | (5) | PROPYLENE GLYCOL | 3 |
| Methyl 4-hydroxybenzoate | (5) | METHYLPARABEN | 0.15 |
| Water, demineralised | | AQUA (WATER) | to 100 |

| Constituents/trade name | Source of supply | INCI | [% by wt.] |
|---|---|---|---|
| C | | | |
| Probiol L 05018 (empty liposomes) | (7) | AQUA, ALCOHOL DENAT, LECITHIN, GLYCERINE, DISODIUM PHOSPHATE | 5 |
| Water, demineralised | | AQUA (WATER) | 10.00 |
| Compound Ia, Ib, Ic, Id or Ie | | | 0.2 |
| | Total | | 100.00 |

Preparation Process

Firstly, phases A and B are warmed to 80° C. Phase B is then slowly added to phase A with stirring and homogenised. The mixture is then cooled, and phase C is added at 40° C.

Sources of Supply (1) Evonik Goldschmidt GmbH, (2) Cognis GmbH, (3) BASF SE, (4) Sasol Germany GmbH, (5) Merck KGaA/Rona®, (6) Dow Corning, (7) Kuhs GmbH & Co. KG Example 10

W/O Formulation

| Constituents/trade name | Source of supply | INCI | [% by wt.] |
|---|---|---|---|
| A | | | |
| Dow Corning 3225 C | (1) | CYCLOMETHICONE, DIMETHICONE COPOLYOL | 23.6 |
| Propyl 4-hydroxybenzoate | (2) | PROPYLPARABEN | 0.05 |
| Compound Ia, Ib, Ic, Id or Ie | | | 0.1 |
| B | | | |
| Methyl 4-hydroxybenzoate | (2) | METHYLPARABEN | 0.15 |
| 1,2-Propanediol | (2) | PROPYLENE GLYCOL | 35.9 |
| Water, demineralised | | AQUA (WATER) | to 100 |
| | Total | | 100.00 |

Preparation Process

Firstly, phase B is dissolved and then added to phase A. The pH is adjusted to the value pH=6.0 using sodium hydroxide solution or citric acid.

Sources of Supply (1) Dow Corning (2) Merck KGaA/Rona®

Example 11

O/W Anti-Ageing Cream with UV A/B Protection

| Constituents/trade name | Source of supply | INCI | [% by wt.] |
|---|---|---|---|
| A | | | |
| Eusolex ® 2292 | (1) | ETHYLHEXYL METHOXYCINNAMATE, BHT | 3 |
| Eusolex ® 4360 | (1) | BENZOPHENONE-3 | 0.5 |
| Tego Care 150 | (2) | GLYCERYL STEARATE, STEARETH-25, CETETH-20, STEARYL ALCOHOL | 8 |
| Lanette O | (3) | CETEARYL ALCOHOL | 1.5 |
| Luvitol EHO | (4) | CETEARYL OCTANOATE | 5 |
| Miglyol 812 N | (5) | CAPRYLIC/CAPRIC TRIGLYCERIDE | 5 |
| Paraffin liquid | (1) | PARAFFINUM LIQUIDUM (MINERAL OIL) | 3 |
| Abil-Wax 2434 | (2) | STEAROXY DIMETHICONE | 1.6 |
| Dow Corning 200 Fluid (350 cs) | (6) | DIMETHICONE | 0.5 |
| Propyl 4-hydroxybenzoate | (1) | PROPYLPARABEN | 0.05 |
| Compound Ia, Ib, Ic, Id or Ie | | | 1 |

-continued

| Constituents/trade name | Source of supply | INCI | [% by wt.] |
|---|---|---|---|
| B | | | |
| 1,2-Propanediol | (1) | PROPYLENE GLYCOL | 3 |
| Methyl 4-hydroxybenzoate sodium salt | (1) | SODIUM METHYLPARABEN | 0.17 |
| Water, demineralised | | AQUA (WATER) | to 100 |
| | Total | | 100.00 |

Preparation Process

Firstly, phases A and B are mixed separately and warmed to 80° C. Phase B is then slowly added to phase A with stirring. The mixture is homogenised cooled to room temperature.

Sources of supply: (1) Merck KGaA/Rona®, (2) Evonik Goldschmidt GmbH, (3) Cognis GmbH, (4) BASF AG, (5) Sasol Germany GmbH, (6)

The invention claimed is:

1. A tanning method comprising:
adding one of more compounds of formula I,

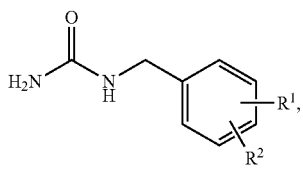

where
$R^1$ and $R^2$ stand, independently of one another, for —H, —OH, -straight-chain or branched O—($C_1$- to $C_6$-alkyl),
where $R^1$ and $R^2$ may also together form an unsubstituted or substituted five-membered ring, in which one or two non-adjacent $CH_2$ groups may be replaced by O and which may be substituted by at least one straight-chain or branched alkyl group having 1 to 6 C atoms,
and/or salts, conformers and/or solvates thereof, including mixtures thereof in all ratios, as a self-tanning substance to a composition to be applied topically, and topically applying said composition to skin of a human, wherein said composition is a face and/or body emulsion, face and/or body oil, powder make-up, emulsion make-up, wax make-up, sunscreen, pre-sun preparation or after-sun preparation.

2. A method comprising topically applying a face and/or body emulsion, face and/or body oil, powder make-up, emulsion make-up, wax make-up, sunscreen, pre-sun preparation or after-sun preparation comprising one or more compounds of formula I to skin of a human,

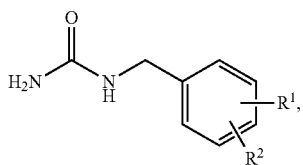

where
$R^1$ and $R^2$ stand, independently of one another, for —H, —OH, -straight-chain or branched O—($C_1$- to $C_6$-alkyl),
where $R^1$ and $R^2$ may also together form an unsubstituted or substituted five-membered ring, in which one or two non-adjacent $CH_2$ groups may be replaced by O and which may be substituted by at least one straight-chain or branched alkyl group having 1 to 6 C atoms,
and/or salts, conformers and/or solvates thereof, including mixtures thereof in all ratios, in an amount sufficient for increasing melanin synthesis, for improving melanin transport and/or for improving distribution of melanin in suprabasal layers.

3. The method according to claim 1, wherein $R^1$ in compounds of formula I stands for H, OH or a straight-chain or branched alkoxy group having 1 to 4 C atoms.

4. The method according to claim 1, wherein $R^2$ in compounds of formula I stands for H, OH or a straight-chain or branched alkoxy group having 1 to 4 C atoms.

5. The method according to claim 1, wherein $R^1$ and $R^2$ in compounds of formula I together form a five-membered ring containing two O atoms, which may be substituted by one or two straight-chain or branched alkyl group(s) having 1 to 6 C atoms.

6. The method according to claim 1, wherein the compound of formula 1 is selected from the compounds of formula Ia to Ie

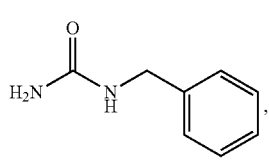

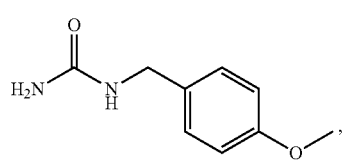

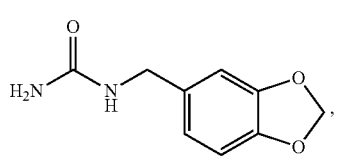

-continued

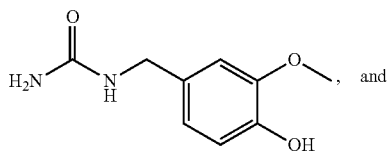
Id

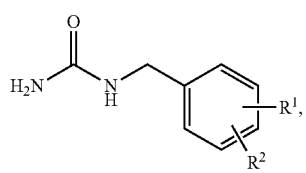
Ie

7. A preparation comprising a vehicle which is suitable for topical application to skin of a human and at least one compound of formula I in an amount of 0.01 to 10% by weight,

I where
R$^1$ and R$^2$ stand, independently of one another, for —H, —OH, -straight-chain or branched O—(C$_1$- to C$_6$-alkyl),
where R$^1$ and R$^2$ may also together form an unsubstituted or substituted five-membered ring, in which one or two non-adjacent CH$_2$ groups may be replaced by O and which may be substituted by at least one straight-chain or branched alkyl group having 1 to 6 C atoms, subject to a proviso that R$^1$ and R$^2$ cannot both be H, and/or salts, conformers and/or solvates thereof, including mixtures thereof in all ratios, wherein said preparation is a face and/or body emulsion, face and/or body oil, lipstick, lip-care stick, powder make-up, emulsion make-up, wax make-up, sunscreen, pre-sun preparation or after-sun preparation.

8. The preparation according to claim 7, wherein at least one further self-tanning substance is present.

9. The method according to claim 2, wherein R$^1$ in compounds of formula I stands for H, OH or a straight-chain or branched alkoxy group having 1 to 4 C atoms.

10. The method according to claim 2, wherein R$^2$ in A compounds of formula I stands for H, OH or a straight-chain or branched alkoxy group having 1 to 4 C atoms.

11. The method according to claim 2, wherein R$^1$ and R$^2$ in compounds of formula I together form a five-membered ring containing two O atoms, which may be substituted by one or two straight-chain or branched alkyl group(s) having 1 to 6 C atoms.

12. The method according to claim 2, wherein the compound of formula 1 is selected from the compounds of formula Ia to Ie

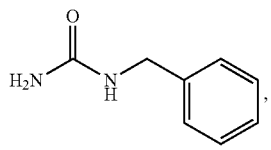
Ia

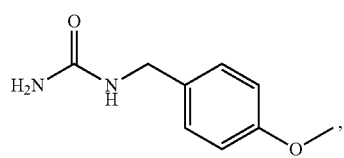
Ib

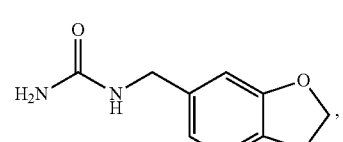
Ic

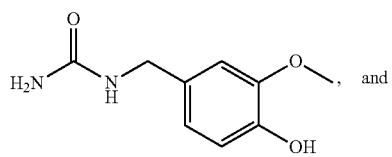
Id

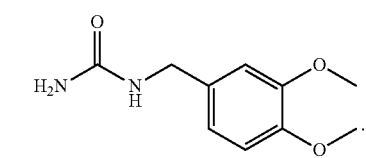
Ie

13. The method of claim 2 comprising topically applying a face and/or body emulsion, face and/or body oil, powder make-up, emulsion make-up, wax make-up, sunscreen, pre-sun preparation or after-sun preparation comprising a compound of formula Ic to skin of a human,

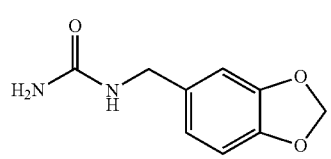
Ic and/or salts, conformers and/or solvates thereof, including mixtures thereof in all ratios, in an amount sufficient for increasing melanin synthesis, for improving melanin transport and/or for improving the distribution of melanin in suprabasal layers.

14. A preparation comprising a vehicle which is suitable for topical application and at least one compound of formula Ic in an amount of 0.01 to 10% by weight,

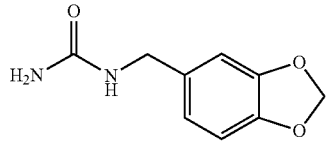

and/or salts, conformers and/or solvates thereof, including mixtures thereof in all ratios, wherein said preparation is a face and/or body emulsion, face and/or body oil, lipstick, lip-care stick, powder make-up, emulsion make-up, wax make-up, A sunscreen, pre-sun preparation or after-sun preparation.

15. The preparation according to claim 14, wherein at least one further self-tanning substance is present.

16. The preparation according to claim 14, in the form of an emulsion.

17. The preparation according to claim 14, which additionally comprises one or more of a preservative, stabilizer, solubilizer, colorant, odour improver, thickener, plasticiser, humectant, interface-active agent, emulsifier, preservative, antifoaming agent, perfume or propellant.

18. The preparation according to claim 14, wherein the vehicle comprises a vegetable fat, vegetable oil, wax, paraffin, paraffin oil, lanolin oil, starch, tragacanth, fatty acid ester, animal fat, fatty alcohol, cellulose derivative, polyethylene glycol, silicone, silicone oil, bentonite, silica, talc, zinc oxide, or a mixture thereof.

* * * * *